United States Patent
Gramann et al.

(10) Patent No.: US 9,227,162 B2
(45) Date of Patent: Jan. 5, 2016

(54) MIXER FOR PREPARING A DENTAL MATERIAL, AND SYSTEM COMPRISING THE SAME

(75) Inventors: Jens Gramann, Grafelfing (DE); Korbinian Schepke-Gerlach, Gauting (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 462 days.

(21) Appl. No.: 13/806,021

(22) PCT Filed: Jun. 21, 2011

(86) PCT No.: PCT/US2011/041185
§ 371 (c)(1),
(2), (4) Date: Mar. 1, 2013

(87) PCT Pub. No.: WO2011/163185
PCT Pub. Date: Dec. 29, 2011

(65) Prior Publication Data
US 2013/0148466 A1   Jun. 13, 2013

(30) Foreign Application Priority Data
Jun. 22, 2010   (EP) .................................... 10166766

(51) Int. Cl.
*B01F 7/00* (2006.01)
*A61C 9/00* (2006.01)

(52) U.S. Cl.
CPC ........... *B01F 7/00633* (2013.01); *A61C 9/0026* (2013.01); *B01F 7/00125* (2013.01); *B01F 7/00141* (2013.01); *B01F 7/00216* (2013.01); *B01F 7/00258* (2013.01); *B01F 2215/0039* (2013.01); *B01F 2215/0431* (2013.01)

(58) Field of Classification Search
CPC .................... B01F 2215/0431; B01F 7/00125; B01F 7/00141; B01F 7/00216; B01F 7/00258; B01F 7/00633; A61C 9/0026
See application file for complete search history.

(56) References Cited

U.S. PATENT DOCUMENTS 6,394,643 B1 * 5/2002 Bublewitz et al. ......... 366/172.1
6,443,612 B1 * 9/2002 Keller ........................... 366/307
(Continued)

FOREIGN PATENT DOCUMENTS

DE   29907573   9/2000
DE   10112904   4/2010
(Continued)

OTHER PUBLICATIONS

English Language Abstract for DE 10112904 dated Apr. 22, 2010.
(Continued)

*Primary Examiner* — Tony G Soohoo (57) ABSTRACT

A mixer (10) for preparing a dental material comprises a mixing barrel (17) and a mixing rotor (16), a mixer inlet (13, 14), and an outlet (15). The mixing rotor is rotatable about a rotation axis (A), and comprises four mixing paddle levels (21, 22, 23, 24) each comprising at least one mixing paddle. The mixing paddle levels are axially disposed over a portion of the mixing rotor with the paddle levels being axially spaced at a generally uniform paddle spacing. The mixing paddles further have a thickness in the dimension parallel to the rotation axis, and the ratio between the paddle spacing and the paddle thickness is at least 2:1, thereby maximizing the mixing efficiency, and minimizing energy consumption.

19 Claims, 4 Drawing Sheets

(56) References Cited

U.S. PATENT DOCUMENTS

| | | | |
|---|---|---|---|
| 6,523,992 B1 * | 2/2003 | Bublewitz et al. | 366/172.1 |
| 6,837,612 B2 * | 1/2005 | Bublewitz et al. | 366/172.1 |
| 7,320,541 B2 * | 1/2008 | Wagner et al. | 366/172.1 |
| D571,479 S * | 6/2008 | Wagner | D24/220 |
| D571,927 S * | 6/2008 | Wagner | D24/220 |
| D617,001 S * | 6/2010 | Lee | D24/220 |
| 7,731,413 B2 * | 6/2010 | Busin et al. | 366/171.1 |
| 7,771,110 B2 * | 8/2010 | Wang | 366/155.1 |
| 2001/0005338 A1 * | 6/2001 | Muhlbauer et al. | 366/307 |
| 2003/0137898 A1 * | 7/2003 | Wagner et al. | 366/172.1 |
| 2004/0085854 A1 * | 5/2004 | Pauser et al. | 366/172.1 |
| 2009/0207685 A1 | 8/2009 | Busin et al. | |
| 2012/0218856 A1 * | 8/2012 | Walter et al. | 366/307 |
| 2013/0148466 A1 | 6/2013 | Gramann et al. | |

FOREIGN PATENT DOCUMENTS

| | | |
|---|---|---|
| EP | 1510249 | 3/2005 |
| EP | 1836992 | 9/2007 |
| EP | 1892033 | 2/2008 |
| WO | WO 98-43727 | 10/1998 |
| WO | WO 03-055582 | 7/2003 |
| WO | WO 2007-041878 | 4/2007 |
| WO | WO 2008-082549 | 7/2008 |
| WO | WO 2009-033832 | 3/2009 |
| WO | WO 2011/163185 | 12/2011 |

OTHER PUBLICATIONS

Extended EP Search Report for EP 10 16 6766 dated Dec. 10, 2010.
PCT International Search Report for PCT/US2011/041185 mailed Sep. 14, 2011.

* cited by examiner

MIXER FOR PREPARING A DENTAL MATERIAL, AND SYSTEM COMPRISING THE SAME

CROSS REFERENCE TO RELATED APPLICATIONS

This application is a national stage filing under 35 U.S.C. 371 of PCT/US2011/041185, filed Jun. 21, 2011, which claims priority to European Application No. 10166766.5, filed Jun. 22, 2010, the disclosures of which are incorporated by reference in their entirety herein.

FIELD OF THE INVENTION

The invention relates to a mixer for preparing a dental material, and in particular to a mixer in which mixing paddle levels are provided at a special generally uniform spacing relative to one another. The invention further relates to a system comprising such a mixer and a mixing device.

BACKGROUND ART

Dental materials are often prepared from mixing individually stored components. There are dental mixing and dispensing devices which can automatically mix components to form a usable dental material, and which can further dispense such a material in suitable portions for use. Typically these dental mixing and dispensing devices have a receptacle for receiving the components, and are typically adapted to continuously supply amounts of the components into a mixer. Within the mixer the materials are normally continuously mixed and dispensed as further components are supplied into the mixer. An exemplary device for mixing and dispensing a dental impression material is for example available under the designation 3M™ ESPE™ Pentamix™ from 3M ESPE AG, Germany.

Because a variety of different types of dental materials are available on the market such a dental mixing and dispensing device desirably can work with various different materials without substantially changing the configuration of the device. However there is a plurality of different mixers on the market which are specifically optimized for mixing certain specific materials or for providing a certain mixing quality. Further often so-called dynamic mixers are used which typically have a mixing rotor which can be motor driven. The mixing rotor is typically arranged in a mixing barrel and mixes the components as they flow though the barrel.

For example EP 1 510 249 discloses a mixer for dental impression material. The mixer has a mixer body accommodating a mixing rod that carries stirring blades. Components of a dental impression material can flow through the body and are mixed by the stirring blades which rotate in a plane laterally to the flow of the components. The blades are arranged at a predetermined positional interval along an axial direction of the rod and at a uniform positional interval circumferentially around the rod. The axial interval between two downstream blades is wider than the axial interval between further upstream blades. Thus the dental impression material gets mixed before it reaches the wider interval where it shall completely fill the space between the stirring rod and the mixer body to avoid air getting included in the mixture.

DE10112904 discloses a dynamic mixer for mixing at least two paste components of different volume proportions. The mixer comprises a housing with at least two inlet openings and at least one outlet opening, a mixer element being rotatably mounted in a mixing chamber of said housing. The housing has at least one delay chamber comprising a limiting wall that blocks the paste stream in the direction of flow and at least one opening that opens into the mixing chamber, said opening(s) being set back in relation to the limiting wall. The mixer is particularly suitable for mixing paste components with a relatively high viscosity of.

There are further mixers on the market. However there is still a desire to provide a mixer which can mix a multiplicity of different materials at sufficient mixing quality. There is further a desire that such a mixer is relatively inexpensive.

SUMMARY OF THE INVENTION

The invention in one aspect relates to a mixer, in particular to a dynamic mixer, for preparing a dental material. The mixer comprises a mixing barrel and a mixing rotor. The mixing rotor is accommodated at least partially within the mixing barrel. Further the mixer comprises at least one mixer inlet, preferably at least two mixer inlets for receiving components of the dental material, and an outlet for releasing a mixture of the components. The mixing rotor is rotatable about a rotation axis of the mixing rotor, and comprises at least four mixing paddle levels. Each of the mixing paddle levels comprises at least one mixing paddle. The mixing paddle levels are disposed over at least a portion of the mixing rotor in a dimension generally parallel to the rotation axis. Further the mixing paddle levels are spaced in the dimension generally parallel to the rotation axis at a generally uniform paddle spacing relative to one another. Further each of the mixing paddles has a thickness in the dimension parallel to the rotation axis, wherein the ratio between the paddle spacing and the paddle thickness is at least 2:1.

A mixing paddle level as referred to in this specification may comprise a group of mixing paddles that are disposed circumferentially around the mixing rotor. The mixing paddles of a mixing paddle level further preferably are substantially co-aligned in a dimension generally parallel to the rotation axis.

The mixer is typically adapted such that during operation of the mixer the mixing paddles typically move in a plane generally transverse to the flow of the components to thereby shear the components. Typically the more intense the shearing, meaning the more often a portion of the components is sheared by a mixing paddle, the more homogeneous is the mixture. It has been found that the shearing typically depends on the rotation speed of the mixing rotor, the flow rate of the components through the mixer (=flow rate of the mixture dispensed), and the number of mixing paddles on the mixing rotor. It has been observed that for example a lower amount of mixing paddles may be compensated by a higher rotation speed of the mixing rotor, if the same flow rate is used. Or a reduced flow rate may be used for compensating a lower number of paddles or a lower rotation speed. It has further been found that a reduction of mixing paddles typically goes along with a reduced mixing homogeneity (based on the same flow rates and rotation speeds).

However the invention preferably allows using a reduced number of mixing paddles relative to a prior art mixer without causing a substantially reduced mixing quality, and without compensating by the rotation speed or the flow rate. The invention is further advantageous in that it preferably enables the use of relative high viscosity materials, in particular with mixing devices having fixed settings of the rotation speed and the flow rate. This is because the mixer of the invention may help avoiding a warming of the material from overly shearing, and thus may help preventing the material from premature hardening (in case a hardenable mixture is prepared). The invention may further be advantageous because it preferably helps minimizing the torque required to rotate the mixing rotor and further the forces required to urge the components to flow through the mixer. The invention may further help minimizing manufacturing costs due to savings of raw material needed for making the mixing rotor.

In one embodiment the ratio between the paddle spacing and the paddle thickness is within a range of 2:1 to 3:1. Further the paddle thickness may be within a range of about 1.8 mm to about 2.2 mm, preferably about 2 mm. The spacing of the mixer paddle levels relative to one another may be within a range of about 3.6 mm to about 6.6 mm, preferably about 4.8 mm. Thus the preferred ratio between the paddle spacing and the paddle thickness is about 2.4:1.

In another embodiment the spaces between the paddle levels is entirely free of mixing paddles. Further the space between two mixing paddle levels may be entirely free from any structure of the mixer. Such a space may be entirely filled with components to be mixed and/or a mixture of the components.

In a further embodiment at least one of the mixing paddle levels has at least two mixing paddles which are axially aligned with one another. Preferably at least one of the mixing paddle levels comprises a plurality of mixing paddles being axially aligned with one another. Such a plurality of mixing paddles may extend radially relative to the rotation axis and may be generally uniformly distributed annularly about the rotation axis of the mixing rotor. For example a mixing paddle level may have four mixing paddles that are angularly arranged relative to one another by about 90 degrees. Further each of the mixing paddle levels may comprise a plurality of axially aligned mixing paddles. Again these mixing paddles of each level may extend radially relative to the rotation axis and may be generally uniformly distributed annularly about the rotation axis. The mixing paddle levels may between one another form an annular ring shaped space which is free of mixing paddles. This space may fill with the components during use of the mixer.

In a further embodiment a mixing paddle of one of the mixing paddle levels is arranged substantially inline with one or more mixing paddles of another one of the mixing paddle levels in a direction parallel to the rotation axis. Thus for example a mixing rotor having four mixing paddle levels each having four mixing paddles may have four rows of mixing paddles within which four paddles are arranged inline with one another, and those four paddle rows may be angularly arranged relative to one another at generally equal angles from one another.

In one embodiment the mixer includes only four uniformly spaced mixing paddle levels. The mixer may have a further mixing paddle level which is spaced from one of the uniformly spaced mixing paddle levels at a different spacing, for example at a smaller or wider spacing. The skilled person will however recognize that such an embodiment still implements the invention.

In one embodiment the mixing rotor comprises a rotor shaft being arranged generally coaxially to the rotation axis. Preferably the mixing paddles protrude from the rotor shaft. The rotor shaft may otherwise be substantially cylindrical. Further the rotor shaft and the mixing barrel together preferably form a passageway for the components of the dental material. Thereby the mixing barrel may form a generally cylindrical inner surface. The inner surface of the mixing barrel may in particular be free of protrusions.

In another embodiment the mixing paddles extend between the rotor shaft and substantially the mixing barrel. Therefore the mixing paddles may extend laterally to the rotation axis through the passageway. Thus components flowing through the passageway may have to flow around the mixing paddles.

In a particular embodiment the mixing paddles protrude from the rotor shaft at a paddle length of between about 3 mm and about 5 mm, and preferably about 4.3 mm. The diameter of the rotor shaft may be within a range of about 4 mm to 6 mm, preferably about 5.3 mm. Therefore the cross-section of the passageway available for the components to flow through may be wide enough to allow components to be urged through the passageway at acceptable forces, but small enough to minimize waste due to components remaining in the mixer after use.

In another embodiment the mixing paddles are tapered in a dimension generally transverse to the rotation axis. The mixing paddles may for example have a width forming a third dimension besides the length and thickness forming first and second dimensions respectively. The paddle width may be within a range of about 1.8 mm to about 2.2 mm, preferably about 2 mm. The mixing paddles may taper in the dimension of the width, for example. The mixing paddles may thus may be streamlined to a certain extend such that the paddles move with the tapered edge leading through the components, when the mixer is used for mixing components. Thereby the torque required to rotate the mixing rotor may be minimized. The taper may comprise a radius or any other suitable shape.

In another embodiment the mixing rotor comprises a coupling for engagement with a drive shaft for driving the mixing rotor. The mixer housing may be adapted such that it can be rotationally retained for rotating the mixing rotor relative to the housing. For example the inlets may be formed as plugs and/or sockets which can be retained at a mixing device.

A further aspect of the invention relates to a system comprising the mixer according to the invention and a mixing device. The mixing device of the system comprises a drive shaft for driving the mixing rotor of the mixer, a receptacle for receiving the components of the dental material, and at least one plunger for urging the components toward the mixer. The mixing device is preferably motorized for automatically driving the mixing rotor and the plunger. Preferably the mixing device is a table top device for use in a dental practice.

In on embodiment the mixing device comprises two plungers, each being adapted for urging one component toward the mixer. The mixing device may further comprise one or more material containers for containing the components. The material container(s) preferably have outlet nozzles. Further the outlet nozzles and the mixer inlets are adapted for connecting the container and the mixer for fluid communication with one another.

In one embodiment the material container(s) comprise(s) components of a dental material which is selected from Polyether or VPS (A-silicone) impression materials of one of the types 0 (putty) to 3 (light body) as specified in ISO 4823. In particular the dental material may be at least one of the materials available under the designation: Permadyne™ Penta™ L, Impregum™ Penta™, Express™ XT Penta™ H, Express™ 2 Penta™ Putty, all available from 3M ESPE AG, Germany.

In another aspect the invention relates to a mixing rotor for use in a mixer for preparing a dental material. Such a mixer comprises a mixing barrel and a mixing rotor. The mixing rotor is adapted to be accommodated at least partially within the mixing barrel. Further the mixer comprises at least two mixer inlets for receiving components of the dental material, and an outlet for releasing a mixture of the components. The mixing rotor is adapted such that it is rotatable about a rotation axis of the mixing rotor, and comprises at least four mixing paddle levels. Each of the mixing paddle levels comprises at least one mixing paddle. The mixing paddle levels are disposed over at least a portion of the mixing rotor in a dimension generally parallel to the rotation axis. Further the mixing paddle levels are spaced in the dimension generally parallel to the rotation axis at a generally uniform paddle spacing relative to one another. Further each of the mixing paddles has a thickness in the dimension parallel to the rotation axis, wherein the ratio between the paddle spacing and the paddle thickness is at least 2:1.

A further aspect of the invention concerns a kit of parts comprising a mixer of the invention and a mixing rotor of the prior art. The mixing rotor of the prior art may be accommodated in a mixer. The kit may further comprise at least one dental material, preferably in the form of individual components. Such a kit may be useful for retrofitting existing mixers of the prior art with a mixing rotor of the invention.

DETAILED DESCRIPTION OF THE INVENTION

Figure 1:
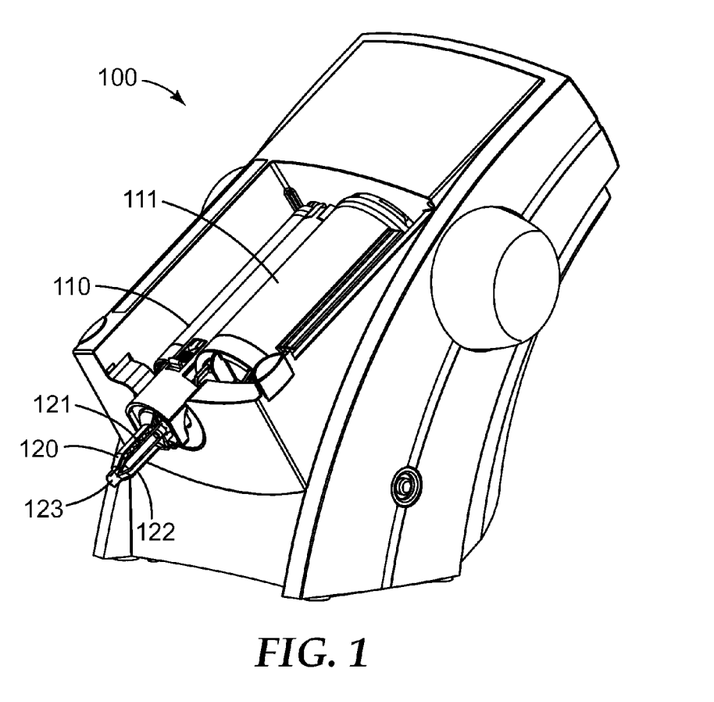
FIG. 1 is a perspective view of a system comprising a mixer according to an embodiment of the invention.

FIG. 1 shows a device 100 for mixing and dispensing dental materials. The device is motorized and therefore allows for automatic dispensation of the materials. The device 100 holds two components of the dental material in containers 110, 111. A mixer 120 for mixing the two components is attached to the device 100. The mixer 120 has a mixing chamber formed between a rotatable mixing rotor 121 and a mixer barrel 122. The mixer is connected with the containers 110, 111 such that the individual components can flow into the mixing chamber. The mixture can exit through an outlet 123 of the mixer 120. The device 100 is adapted to drive the mixing rotor 121 for mixing the components in the mixing chamber. The device 100 implements a continuous dynamic mixing process in which components can be continuously supplied into the mixing chamber and in which the mixture from the components can be dispensed continuously from the mixer. Thus the device allows preparation for variable amounts of dental materials without the need of pre-determining amounts of initial components of the mixture. The components can be advanced toward the mixer 120 by a piston (not shown) of the device 100. Both the mixer and the piston can be driven by a motor, or individual motors, in the device 100.

The device shown may be used to mix and dispense a hardenable dental impression material, for example. The mixed material may be used to fill a dental tray which is then placed into a patient's mouth to take a dental impression. The mixer is attached replaceably at the device 100. Therefore when the mixed material hardens and thus blocks the mixer the used mixer may be replaced by an unused mixer for the next use of the device.

Figure 2:
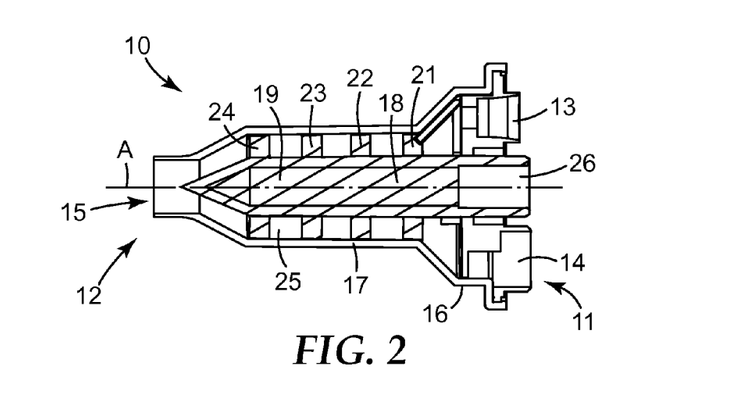
FIG. 2 is a cross-sectional view of a mixer according to an embodiment of the invention.

FIG. 2 illustrates in a cross-sectional view the basic configuration of a mixer 10 according to the invention. The mixer 10 has a rear end 11 and a front end 12, and comprises adjacent the rear end 11 a first inlet 13, and a second inlet 14. Adjacent the front end 12 the mixer comprises an outlet 15. The mixer 10 comprises a mixer housing 16 which preferably forms a mixing barrel 17. In the example the mixing barrel forms an elongated tube which is at least inwardly generally cylindrical. Further the mixer 10 comprises a mixing rotor 18 which is accommodated in the mixing barrel 17 of the mixer 10, and which is rotatable about a rotation axis A. In the example the rotation axis A and the mixing barrel 17 are generally concentric relative to one another. The mixing rotor 18 has a mixing portion 19 which carries four levels 21, 22, 23, 24 of mixing paddles. Each level 21/22/23/24 of mixing paddles comprises at least one mixing paddle, however in the example each level of mixing paddles comprises four mixing paddles which are uniformly distributed circumferentially around the mixing portion 19 (and about the rotation axis A). Further the mixing paddles protrude radially outwardly from the mixing portion 19 and extend with their free ends substantially to the mixing barrel 17. A small space or play may be provided between the free ends of the mixing paddles and the mixing barrel to avoid friction between the paddles and the barrel. A passageway 25 is provided between the mixing portion 19 and the mixing paddles, which allows components supplied into the mixer 10 to flow through the mixing barrel 17.

In operation of the mixer 10 material components may be supplied into the mixer through the first and second inlets 13, 14. Ongoing supply of components preferably causes the components to flow from the inlets 13, 14, through the passageway 25, and toward the outlet 15. The flow direction of the components is substantially parallel to the rotation axis A of the mixing rotor 18. Further preferably the mixing rotor 18 is rotated such that the mixing paddles move in planes that are generally transverse to the rotation axis. Thereby the components are sheared laterally to their flow and caused to mix as they flow toward the outlet.

The mixing rotor 18 can be driven by a motor (not shown). Therefore the mixing rotor has a coupling 26 for engaging with a drive shaft of a mixing and dispensing device. The coupling in the example shown is a receptacle having a polygonal (for example hexagonal) cross-section. However the skilled person will recognize a variety of other configurations enabling an engagement between the mixing rotor 18 and a drive shaft.

Figure 3:
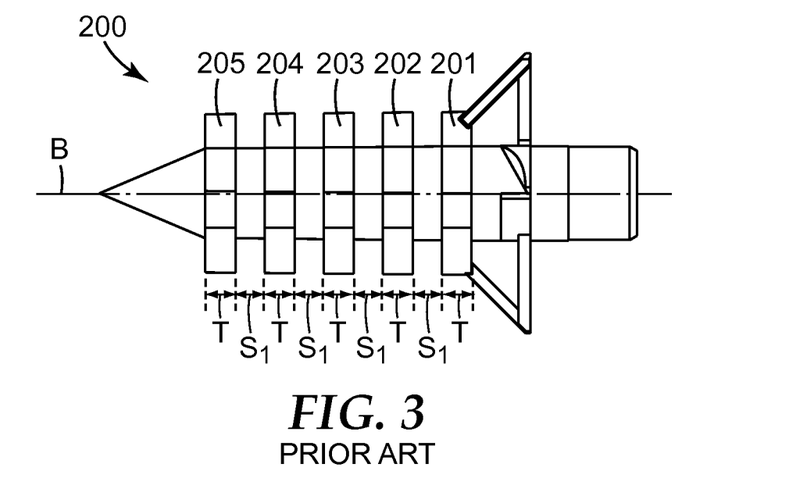
FIG. 3 is a side view of a mixing rotor of a mixer according to prior art.

FIG. 3 shows a mixing rotor 200 according to prior art. The mixing rotor 200 has five levels 201, 202, 203, 204, 205 of mixing paddles. The five levels 201, 202, 203, 204, 205 of mixing paddles are uniformly spaced at a spacing S1 relative to one another in a direction along a rotation axis B of the mixing rotor 200. Each of the mixing paddles further has a thickness T which is a dimension parallel to the rotation axis B.

Figure 4:
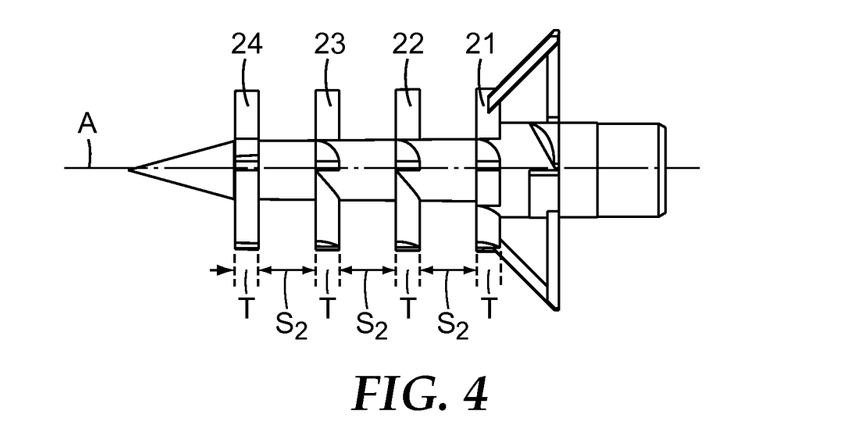
FIG. 4 is a side view of a mixing rotor of a mixer according to an embodiment of the invention.

In contrast FIG. 4 shows the mixing rotor 18 according to the invention which has only four levels 21, 22, 23, 24 of mixing paddles. The four levels 21, 22, 23, 24 of mixing paddles are uniformly spaced at a spacing S2 relative to one another in a direction parallel to a rotation axis A of the mixing rotor 18. Further each paddle has the thickness T. However, relative to the configuration shown in FIG. 3 in this example the spaces between the individual levels of mixing paddles are about twice as wide as the spaces of the mixing rotor of the prior art.

EXAMPLE 1

A mixer having a mixing rotor according to prior art was used to mix a sample from components of a dental impression material. The used impression material is available under the designation Impregum™ Penta™ from 3M ESPE AG, Germany. The mixer was configured as shown in FIG. 2, but was provided with the mixing rotor according prior art (as shown in FIG. 3) instead of the mixing rotor illustrated in FIG. 2.

The mixer was used with a mixing and dispensing device as it is available under the designation 3M™ ESPE™ Pentamix™ 2 from 3M ESPE AG, Germany.

The device and the mixer were used to prepare the sample by mixing the components and dispensing the mixture in the form of a strand on a pad. Thereby the mixing rotor was driven at a speed of about 380 rounds per minute relative to the remainder of the mixer. Further the flow rate of the components through the mixer was maintained at about 72 ml per minute during dispensing the sample. An initial portion of the mixture was discarded to provide a strand that was mixed during a steady state mixing phase. The reaching of the steady state mixing phase was visually assessed by an operator. The components of the impression material were provided in a differently colored form so that a constant mixing quality (indicating the steady state mixing phase) could be recognized visually by the operator from the mixture having a generally uniform combination color.

After the dispensed strand of material had cured the strand was cut generally laterally to the direction at which the strand was dispensed. The cut surface was inspected for color cords resulting from insufficiently mixed or unmixed components. Typically the presence of more and/or more intense color cords on the cut surface is also indicative of more inhomogeneous mixing. Further a more uniform color of the cut surface is typically indicative of a more homogeneous mixing.

Figure 5A:
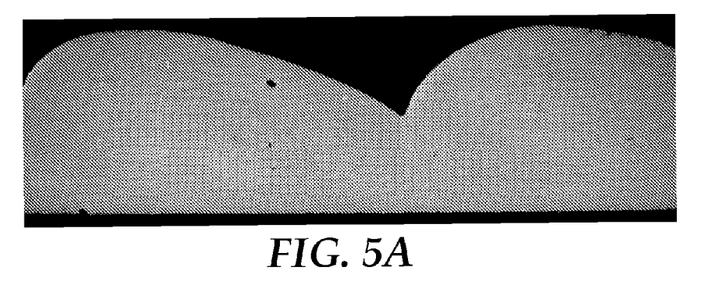
FIG. 5A-5D are photos showing cut surfaces of hardened strands of materials that were mixed using a mixing rotor of the prior art or modified mixing rotors of the prior art.

The cut surface which resulted from the Example 1 is shown in FIG. 5A. The cut surface appears to be of a generally uniform color which indicates a generally homogeneous mixing.

COMPARATIVE EXAMPLE 1.1

The Example 1 was repeated but with a mixing rotor that was generally identical to the mixing rotor of the prior art, but having only four levels of mixing blades. This was achieved by removing one level of mixing paddles from a mixing rotor of the prior art.

Figure 5B:
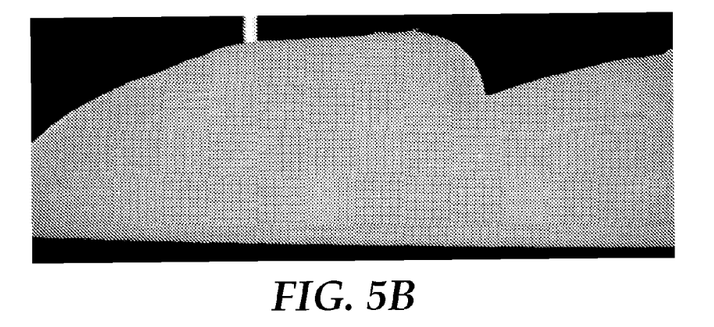

The cut surface which resulted from the Comparative Example 1.1 is shown in FIG. 5B. Relative to the Example 1 the sample of Comparative Example 1.1 exhibits visible color cords on the surface. Therefore it can be assumed that the mixing was less homogeneous than in Example 1.

COMPARATIVE EXAMPLES 1.2 AND 1.3

In Comparative Example 1.2 the Example 1 was repeated but with a mixing rotor having only three levels of mixing blades, and further in Comparative Example 1.3 the Example 1 was repeated with a mixing rotor having only two levels of mixing blades. Again mixing paddles have been removed to reduce the number of mixing paddle levels of a mixing rotor of the prior art so that only the number of mixing paddle levels was different relative to the Example 1 and between the different Comparative Examples.

Figure 5C:
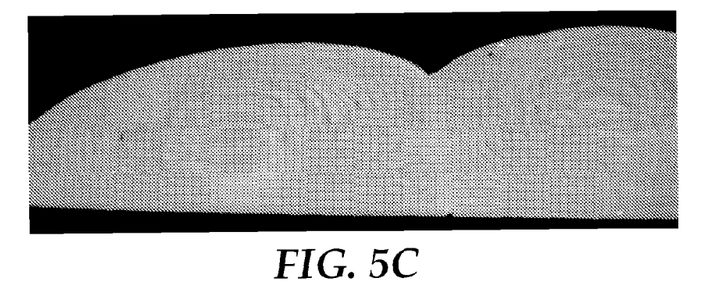
Figure 5D:
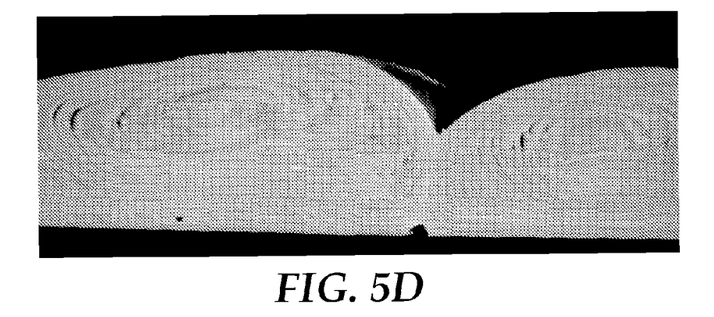

The cut surface resulting from the Comparative Example 1.2 is shown in FIG. 5C and the cut surface resulting from the Comparative Example 1.3 is shown in FIG. 5D. Together with the Comparative Example 1.1 it can be clearly seen that a lower number of mixing paddle levels causes a more distinctive presence of color cords. Accordingly it can be concluded that a lower number of mixing paddle levels causes a less homogeneous mixing.

COMPARATIVE EXAMPLE 2

The Example 1 was repeated but with a mixing rotor of the invention having four levels of mixing paddles. Thus relative to the Example 1 the mixing rotor in Comparative Example 2 has a lower number of mixing paddle levels. Further the mixing paddle levels were spaced at a ratio of 2:1 (spacing of paddle levels relative to paddle thickness). Otherwise the mixing rotor and the remainder of the mixer were unchanged relative to the Example 1.

Figure 6A:
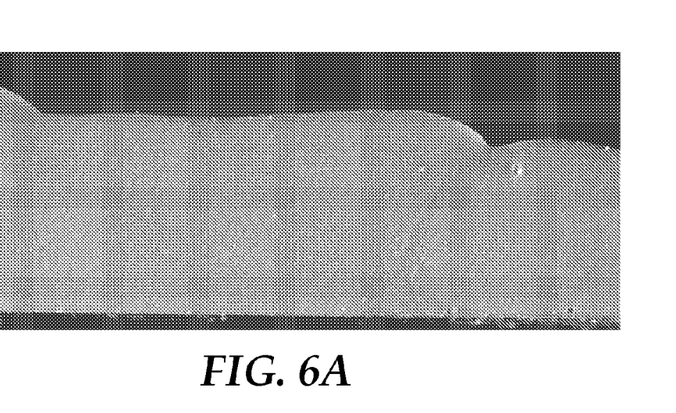
FIGS. 6A, 6B are photos showing cut surfaces of hardened strands of a material that were mixed using a mixing rotor according to an embodiment of the invention.

As it was shown above a reduced number of mixing paddle levels typically results in a less homogeneous mixing, however, surprisingly the mixing rotor of the invention provides a similar homogeneous mixing as the prior art rotor, although the mixing rotor of the invention has only four paddle levels instead of five paddle levels as required for a similar result in the prior art. This can be seen from the cut surface resulting from Comparative Example 2 (shown in FIG. 6A) which generally corresponds to the cut surface of the Example 1 (FIG. 5A).

Figure 6B:
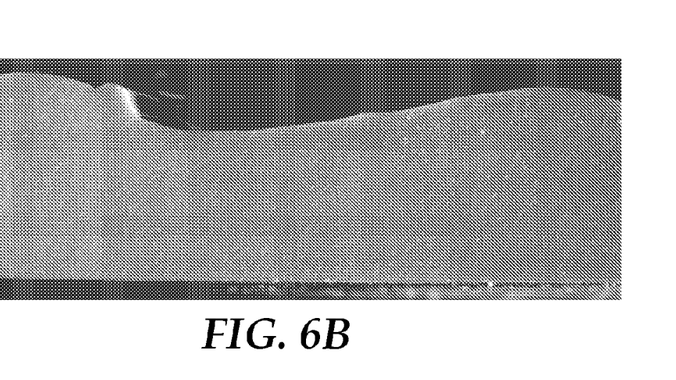

To confirm that this effect is independent from a specific material the Example 1 and Comparative Examples 1.1-1.3 as well as Comparative Example 2 have been repeated with the following dental materials: Permadyne™ Penta L (base component no. 381149/catalyst component no. 381152), Impregum™ Penta, (base component no. 381224/catalyst component no. 381542), Express™ XT Penta H (base component no. 392200/catalyst component no. 321397), Express™ 2 Penta Putty (base component no. 380505/catalyst component no. 378889). The same Examples and Comparative Examples were further repeated with a different dispensing device as it is available under the designation 3M™ ESPE™ Pentamix™ 3 from 3M ESPE AG, Germany. This dispensing device was used with the following parameters: flow rate of dispensed mixture=145 ml per minute, rotation speed of mixing rotor=768 rounds per minute. Similar results have been achieved from these repetitions. FIG. 6B shows a sample which was obtained from repeating the Comparative Example 2, however with a 3M™ ESPE™ Pentamix™ 3 device being used instead of the 3M™ ESPE™ Pentamix™ 2 device. Thus it has been demonstrated that the effect of the invention is independent from the mixed material, the dispensing device and the mixing parameters, but is dependent on the spacing between the mixing paddle levels.

The invention claimed is:
1. A mixer, comprising:
a mixing barrel, and a mixing rotor accommodated at least partially within the mixing barrel,
an inlet, and
an outlet,
the mixing rotor being rotatable about a rotation axis of the mixing rotor, and consisting essentially of four mixing paddle levels each comprising at least one mixing paddle,
the four mixing paddle levels being disposed over at least a portion of the mixing rotor in a dimension substantially parallel to the rotation axis and being spaced relative to one another at a substantially uniform paddle spacing, each of the mixing paddles having a thickness in the dimension substantially parallel to the rotation axis, wherein the ratio between the paddle spacing and the paddle thickness is greater than 2:1.

2. The mixer of claim 1, wherein the ratio between the paddle spacing and the paddle thickness is no greater than 3:1.

3. The mixer of claim 2, wherein the paddle thickness is within a range of 1.8 mm to 2.2 mm.

4. The mixer of claim 1, wherein at least one of the four mixing paddle levels has at least two mixing paddles which are axially aligned with one another.

5. The mixer of claim 1, wherein at least one of the four mixing paddle levels comprises a plurality of mixing paddles being axially aligned with one another.

6. The mixer of claim 1, wherein each of the four mixing paddle levels comprises a plurality of axially aligned mixing paddles, the mixing paddles of each level extending radially relative to the rotation axis and being uniformly distributed annularly about the rotation axis.

7. The mixer of claim 1, wherein a mixing paddle of the four mixing paddle levels is in-line with one or more mixing paddles of another of the four mixing paddle levels in a direction parallel to the rotation axis.

8. The mixer of claim 1, wherein the mixing rotor comprises a rotor shaft arranged coaxially to the rotation axis, wherein the mixing paddles protrude from the rotor shaft, and wherein the mixer comprises a passageway formed by the rotor shaft and the mixing barrel.

9. The mixer of claim 8, wherein the mixing paddles extend between the rotor shaft and the mixing barrel.

10. The mixer of claim 8, wherein the mixing paddles protrude from the rotor shaft at a length of between 3 mm and 5 mm.

11. The mixer of claim 10, wherein the mixing paddles have a width.

12. The mixer of claim 11, wherein the mixing paddles are tapered in the dimension of the width.

13. The mixer of claim 1, wherein the mixing paddles are tapered in a dimension transverse to the rotation axis.

14. The mixer of claim 1, wherein the mixing rotor comprises a coupling for engagement with a drive shaft for driving the mixing rotor.

15. A system comprising the mixer of claim 1 and a mixing device, the mixing device comprising a drive shaft for driving the mixing rotor, a receptacle, and at least one plunger.

16. The system of claim 15, wherein the mixing device further comprises a material container or material containers, the material container(s) having outlet nozzles, wherein the outlet nozzles and the inlets of the mixer are adapted for connecting the container and the mixer for fluid communication with one another.

17. The system of claim 15, wherein the mixing device comprises two plungers, each adapted to urge one component of a dental material toward the mixer.

18. The mixer of claim 1, further comprising a mixing paddle lever level spaced from one of the four mixing paddle levels at a spacing different from the uniform paddle spacing.

19. The mixer of claim 1, wherein there is a space between one end of the mixing paddles and the mixing barrel.

* * * * *